United States Patent [19]
Trozzo et al.

[11] Patent Number: 5,406,265
[45] Date of Patent: Apr. 11, 1995

[54] REMOTE TRANSMITTING FENCELINE MONITORING APPARATUS

[75] Inventors: David L. Trozzo; Daniel A. Nadzam, both of Pittsburgh; Frank T. Paolo, Jr., Leechburg, all of Pa.

[73] Assignee: Geraghty & Miller, Inc., Denver, Colo.

[21] Appl. No.: 989,969

[22] Filed: Dec. 14, 1992

Related U.S. Application Data

[63] Continuation of Ser. No. 665,258, Mar. 6, 1991, abandoned.

[51] Int. Cl.6 .............................................. G08B 17/10
[52] U.S. Cl. .................................... 340/632; 340/693; 73/31.02
[58] Field of Search ............... 340/632, 539, 633, 634, 340/627, 693; 250/338.5; 73/23.2, 31.01, 31.02, 31.03

[56] References Cited
U.S. PATENT DOCUMENTS

| | | | |
|---|---|---|---|
| 4,063,446 | 12/1977 | Fuhrmann | 73/1 G |
| 4,088,986 | 5/1978 | Boucher | |
| 4,363,031 | 12/1982 | Reinowitz | 340/539 |
| 4,443,793 | 4/1984 | Hall, Jr. | 340/634 |
| 4,464,653 | 8/1984 | Winner | 340/501 |
| 4,526,028 | 7/1985 | Hubner | 73/23 |
| 4,572,900 | 2/1986 | Wohltjen | 436/151 |
| 4,651,141 | 3/1987 | Kimura | 340/634 |
| 4,665,385 | 5/1987 | Henderson | 340/632 X |
| 4,959,637 | 9/1990 | Woods et al. | 340/539 |
| 4,999,498 | 3/1991 | Hunt et al. | 250/338.5 |

*Primary Examiner*—Jeffery A. Hofsass
*Attorney, Agent, or Firm*—Standley & Gilcrest

[57] ABSTRACT

An apparatus placed at the "fenceline" (perimeter) of a site, to detect the possible existence of contaminants within the air and transmit an audio signal to a remote location indicating an irregularity in the air quality. Conventional audio transmitters such as a walkie-talkie may be used to detect an audio alarm signal from the contamination detection device and be received by a receiver, such as another walkie-talkie at a remote location. The monitoring system may be housed in a portable enclosure to protect the equipment from weather, vandalism or theft.

6 Claims, 2 Drawing Sheets

REMOTE TRANSMITTING FENCELINE MONITORING APPARATUS

This is a continuation of U.S. patent application Ser. No. 07/665258, filed Mar. 6, 1991, now abandoned.

BACKGROUND AND SUMMARY OF THE INVENTION

The present invention relates generally to gas, vapor and particulate detection devices, and more particularly, to a remote transmitting gas, vapor and/or particulate monitor apparatus that may be used as a warning device for site remediation.

Gases and vapors may be sensed by an organic vapor monitor as is known in the art. Traditionally, the monitoring of gases and vapors has been performed manually with hand-held gas and vapor detectors. The hand-held devices require constant operator attention. Since more than one detector may be needed at a site, the hand-held units would each require an operator and the expense to the site owner would rise accordingly. Additionally, when operators are in or near a contaminated site using the detectors, there may be a potential health hazard to the operators. The "fenceline" is the border or perimeter around a site within which exists potentially contaminated conditions and outside of which is considered to be safe or below some predetermined designated health level. The goal of fenceline monitoring is to ensure that only air of acceptable quality impacts the downwind population. In the course of site remediation, there often exists the potential for volatile organic compound or inorganic compound or other toxic gas or particulate release via the air pathway. Monitoring of potential releases is typically the responsibility of the site health and safety officer who, in addition to protection of on-site worker safety, must protect public health from exposure to site-derived contaminants.

Traditional compound-specific air characterization work is often performed prior to remediation as part of the initial remedial investigation to determine the type and concentration of compounds in the vicinity of the site. These background air investigations are useful in assessing site air quality under existing conditions and are often the only reliable source of data for subsequent risk evaluations performed for the air pathway. During implementation of a chosen remedial technology, compound-specific upwind/downwind ambient air sampling may be performed to assess the potential for air quality degradation attributable to the clean-up effort. While the compound-specific data provided by sampling is indispensable in characterizing the health impact of the site relative to the air pathway, these methods are not applicable to the on-going daily monitoring required during clean-up. In addition to the need for trained air pollution professionals with specialized test equipment on site, the analytical costs over time would be prohibitive and test results would not be available in a suitable time frame to protect the public from an acute release. Therefore, there is a need for a reliable real time air monitoring system which could be operated by site personnel at a reasonable cost during extended site remediation.

The present invention, a remote transmitting fenceline monitor apparatus is designed to fill this need. The monitor may include an organic vapor monitor that utilizes a photoionization detector or in an appropriate application a real time particulate sampler or other gas vapor monitor utilizing alternate sensors. These items and equivalent or similar devices may be purchased off the shelf to measure a wide range of organics, inorganics and particulates. The monitor may contain means for producing a signal, such as an alarm, which triggers when a predetermined health action level has been met. Health action levels are selected based on the specific compound types and concentration derived from the previously performed air characterization study. The known health impact and published threshold limit values or permissible exposure limits are also considered in selecting a health action limit representative of the anticipated group of site compounds in the air.

Unique circuitry may be added to the monitor which permits the organic vapor monitor, particulate sampler or other measurement device to transmit an alarm signal via a transmitter such as a walkie-talkie without operator intervention. Therefore, at the potentially contaminated site, an on-site operator is not needed once the equipment has been set up. By providing a health and safety officer with a second receiver (e.g.-walkie-talkie) of the same frequency, perimeter air quality can be monitored within the transmitting range, on or off site. Other transmitting means may also be used to convey the signal to a remote location. The monitors may be portable, and contained in a weather-proof enclosure capable of extended operation through a rechargeable battery.

Fenceline monitors are usually deployed on the downwind site perimeter as a buffer between the active area of remediation and the general population. In addition to daily calibration with a standard reference gas or by other suitable means, the fenceline monitors may be maintained downwind by either monitoring data from an on-site meteorological station, by observing a windsock, or by listening to local weather reports. Alternatively the fenceline monitors may be sited at multiple locations to encircle the site. The adjustable alarm may be supplemented by an internal data logger which enables storage of data points at predetermined time intervals. This feature provides the added benefit of storage and summarization of ambient concentrations. Such information may be retrieved at a later date and used to demonstrate acceptable perimeter air quality to the public and regulatory officials on an on-going basis.

The foregoing and other objects and advantages will become more apparent when viewed in light of the accompanying drawings and following detailed description.

DESCRIPTION OF PREFERRED EMBODIMENTS(S)

Figure 1:
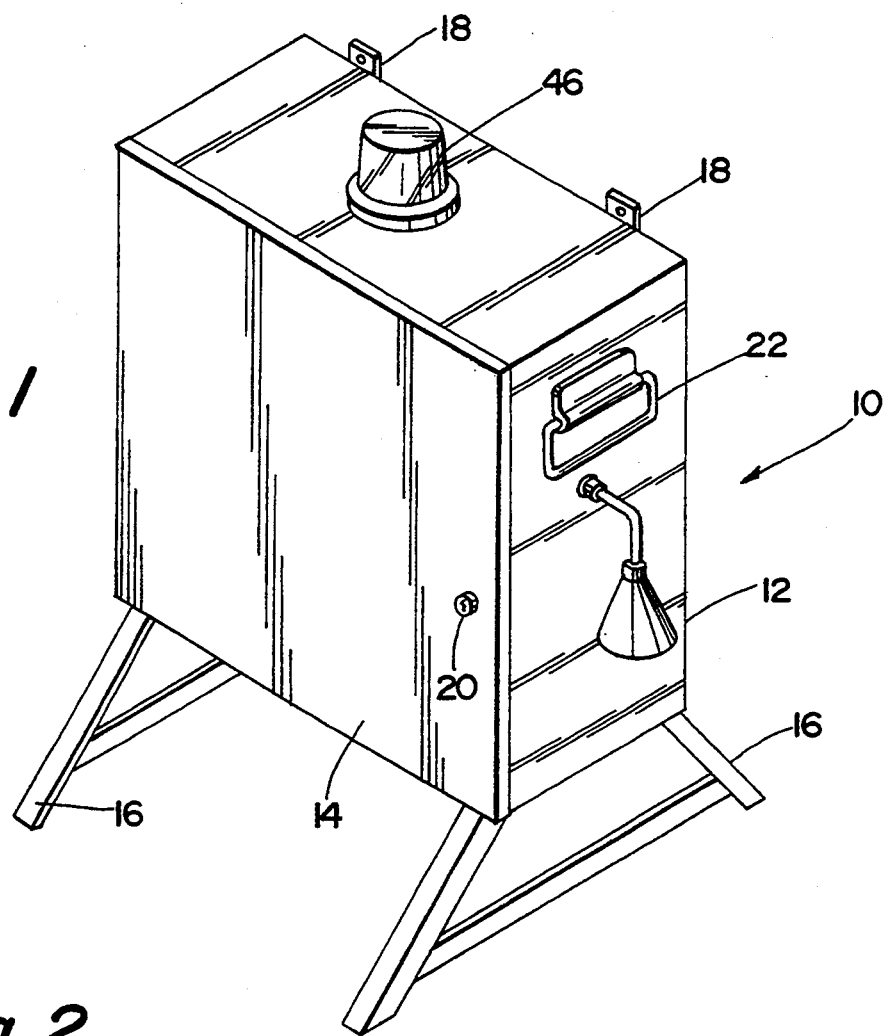
FIG. 1 is a perspective view of the monitoring apparatus of the present invention.

Referring now to the drawings, and particularly FIG. 1, there is illustrated a gas/vapor monitor or a particulate sampler and warning apparatus generally indicated at 10. The assembly 10 may be better seen in FIG. 2 which shows the enclosure 12 having the front panel 14 open.

At remediation sites or other potential sources of contamination, irregularities in air quality may occur as a result of contaminants being released into the air at the site either through naturally occurring releases such as vaporization and wind born entrainment or due to clean-up efforts. The present invention may be used to monitor air quality in and around the contaminated site. The enclosure 12 is provided to protect the monitoring/transmitting equipment from the weather and possible theft or vandalism. The enclosure 12 may be equipped with legs 16 for standing the apparatus 10 on the ground. The enclosure 12 may also have brackets 18 for mounting on a wall. A key lock 20 or other locking means may be provided on panel 14. Handles 22 may be provided to assist in transporting the apparatus 10.

Figure 2:
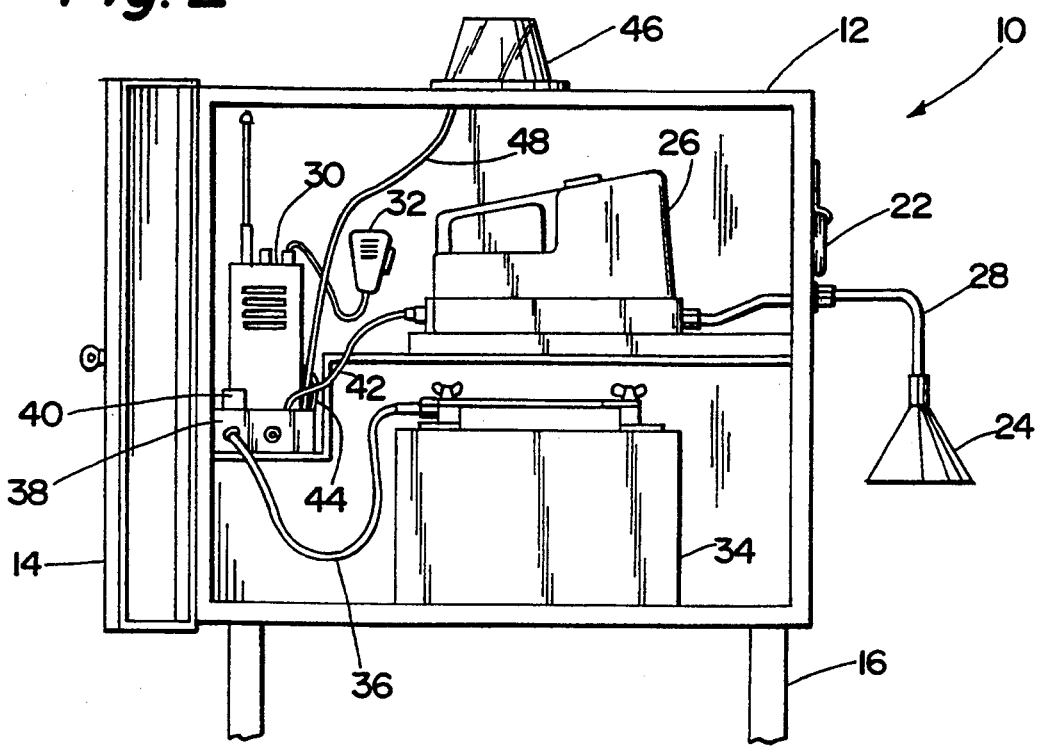
FIG. 2 is an elevation view of the monitoring apparatus shown with the front panel open.

FIG. 2 shows the particular equipment which may be used to complete the apparatus 10. The apparatus 10, requires means for capturing air samples to be monitored while excluding precipitation. A funnel 24 would serve this purpose. An organic vapor monitor or particulate sampler or other appropriate analyzer 26 with an internal adjustable alarm (for example, Thermo Environmental OVM model 580B or equivalent) is equipped to receive air samples from the funnel 24 by means of a tube 28, for example. An audio transmitter, such as an FM walkie-talkie 30 or CB radio, is wired to transmit the alarm signal from the organic vapor analyzer 26 when an alarm condition is reached. A microphone 32 may be used with a walkie-talkie 30 to transmit the alarm signal.

Means for providing power to the circuit will be needed. In a preferred embodiment of the present invention a 12-volt battery 34 provides sufficient power to the system without need for frequent recharging. The power source 34 supplies current through a wire 36 to a radio base and central distribution box 38. A conditional input/output device 40 is connected in circuit to the central distribution box 38 and the organic vapor analyzer 26 or other sensing device to sense irregular signal voltages from the organic vapor monitor or other sensing device 26 indicating an alarm condition. A wire 42 leads from the organic vapor monitor or other sensing device 26 to the central distribution box 38. A wire 44 from the central box 38 leads to the audio transmitter 30. A vent cap 46 may be provided on the enclosure 12 for venting of gases that may build up within the enclosure 12. The circuitry could also have a wire 48 that would lead to an exterior warning light (not shown) so that when the vapor analyzer 26 detects air irregularities not only would the audio transmitter 30 send an audio signal to a receiver (not shown) but also the warning light may be of a type that would be visible from a distance to indicate exactly which monitoring apparatus 10 had detected the irregularity.

Figure 3:
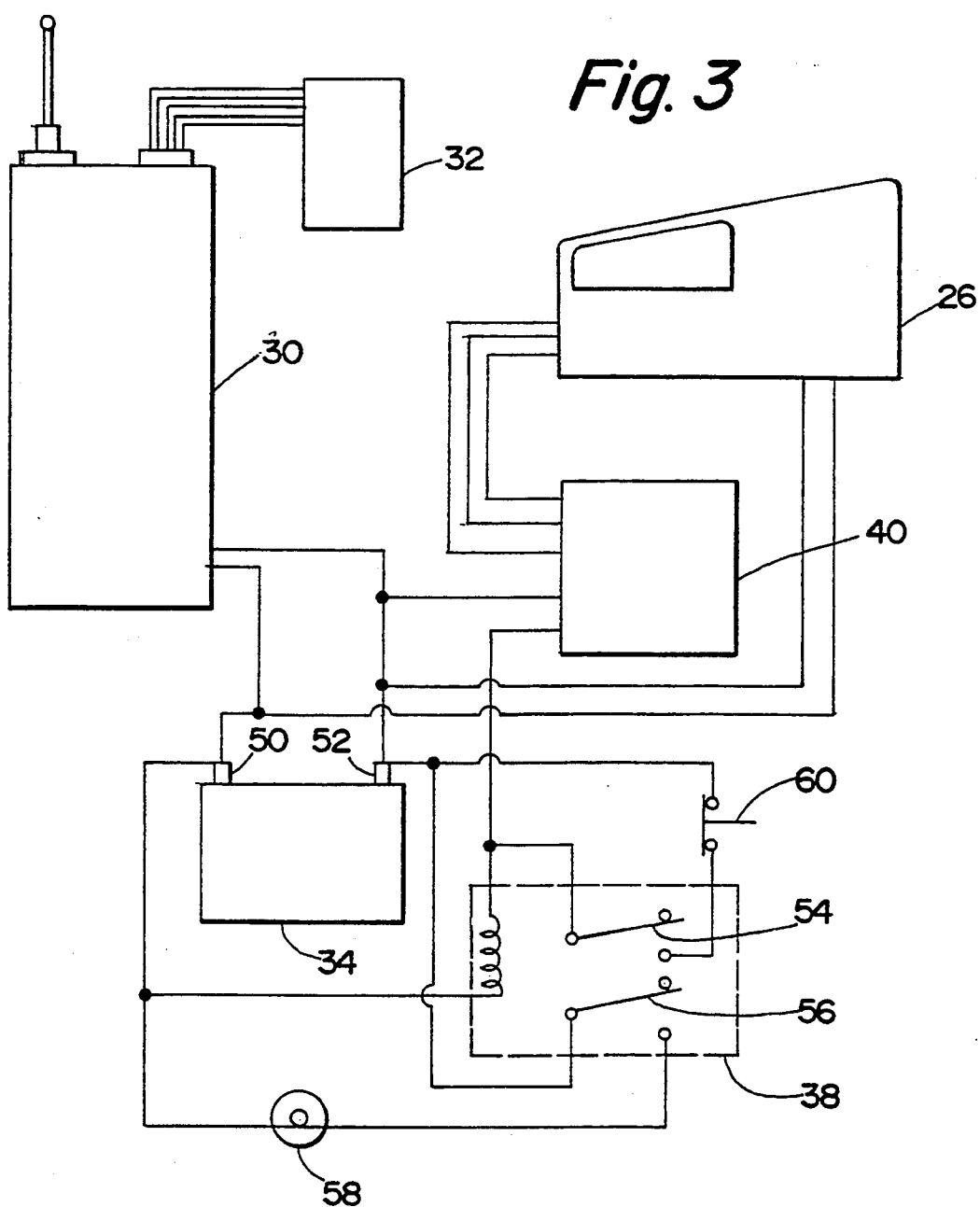
FIG. 3 is a schematic view of the circuitry of the present invention.

Referring now to FIG. 3, there is illustrated a schematic representation of a preferred wiring circuit according to the present invention. It should be recognized that other circuit arrangements may be used in the appropriate application that would fall within the scope of the present invention. A battery 34 is shown with a positive terminal 52 and a negative terminal 50. The battery 34 may be used to supply current to the audio transmitter 30 and the organic vapor analyzer 26. A conditional input/output device 40 is placed in the circuit to provide a closure voltage upon receipt of an irregular signal condition from analyzer 26. The device 40 is powered by the power source 34. The device 40 may be a solid state device, transistor, or relay. In one preferred embodiment of the present invention device 40 may be an I/O Buffered Output Microprocessor module made by the Crydom Company, stock number 62F812. Equivalent devices may also be used and fall within the scope of the present invention.

When the analyzer 26 detects irregularities in the air, it sends a current through the wire causing the switches 54, 56 (which are shown open) to close. With the switches 54, 56 closed, the circuit is completed causing an external resistance 58, such as a horn, light, or other active resistance to go on. A push button switch 60 is provided, when pushed, to deactivate the resistance element 58.

Figure 4:
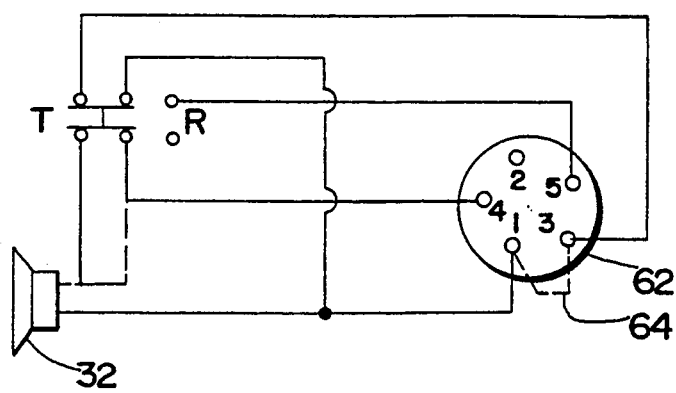
FIG. 4 is a schematic view of the microphone switch in FIG. 3.

Because the audio transmitter 30 is not hand held in the present invention, it must be wired to be a transmitter only and not a receiver. FIG. 4 shows a schematic representation of a transmit only circuit for the walkie talkie 30 shown in FIG. 3. In this particular embodiment, the microphone 32 is wired to the transmitter 30 via a five pin connection 62. A jumper 64 may be provided between pins 1 and 3 to transmit only.

It is thought that the fenceline monitoring apparatus of the present invention and many of its attendant advantages will be understood from the foregoing description. It will be apparent that various changes may be made in the form and construction of the components thereof without departing from the spirit and scope of the invention or sacrificing all of its material advantages, the form hereinbefore described being merely a preferred or exemplary embodiment thereof.

What is claimed is:

1. A system for monitoring air samples for potentially unacceptable levels of contaminants and communicating to a remote location when contaminates are detected, the system comprising:

a contaminant detection device adapted to collect air samples at a remediation site and to analyze said air samples directly, while at said site, to determine if contaminants exist in the air samples;

an audio signal generator connected to said detection device for producing an audio signal instantaneously when the detection device indicates that unacceptable contamination levels exist in the air samples;

an automatic audio transmitter for transmitting said audio signal to a remote location;

a remote audio receiver for receiving said audio signal from said transmitter, independent of any direct physical connection between said audio receiver and said transmitter, and alerting an individual who hears said audio signal at said audio receiver that the contamination signal has occurred at the detection device; and a portable weatherproof enclosure including an exterior warning means visible from a distance suitable for stand alone usage in an outdoors environment independent of the need for human operator intervention, within which said audio signal generator, said audio transmitter and said contamination detection device are contained.

2. The system of claim 1, wherein the means for transmitting is a walkie-talkie having a transmit only circuit.

3. The system of claim 1, wherein the contamination detection device is an organic vapor monitor.

4. The system of claim 1, wherein the contaminant detection device is an inorganic gas vapor monitor.

5. The system of claim 1, wherein the audio transmitter includes a transmit only circuit arrangement.

6. The system of claim 2, wherein the audio receiver is a second walkie-talkie.

* * * * *